United States Patent
Vesey et al.

(10) Patent No.: US 7,374,904 B2
(45) Date of Patent: *May 20, 2008

(54) PRODUCTS CONTAINING QUANTUM OF BIOPARTICLES AND METHOD FOR PRODUCTION THEREOF

(75) Inventors: Graham Vesey, Hornsby (AU); Mark Gauci, French Forest (AU)

(73) Assignee: BTF Pty Ltd, New South Wales (AU)

( * ) Notice: Subject to any disclaimer, the term of this patent is extended or adjusted under 35 U.S.C. 154(b) by 373 days.

This patent is subject to a terminal disclaimer.

(21) Appl. No.: 10/488,683

(22) PCT Filed: Sep. 4, 2002

(86) PCT No.: PCT/AU02/01216

§ 371 (c)(1),
(2), (4) Date: Sep. 22, 2004

(87) PCT Pub. No.: WO03/020959

PCT Pub. Date: Mar. 13, 2003

(65) Prior Publication Data

US 2005/0032192 A1    Feb. 10, 2005

Related U.S. Application Data

(63) Continuation-in-part of application No. 09/949,860, filed on Sep. 12, 2001, now Pat. No. 6,780,581.

(30) Foreign Application Priority Data

Sep. 5, 2001    (AU) .................................. PR7505

(51) Int. Cl.
*C12Q 1/24*    (2006.01)

(52) U.S. Cl. .................. 435/30; 435/29; 435/7.32; 435/4

(58) Field of Classification Search .................. 435/4, 435/5, 7.1, 7.2, 7.32, 29, 30, 239; 436/63, 436/260, 518, 523, 546
See application file for complete search history.

(56) References Cited

U.S. PATENT DOCUMENTS 3,655,838 A    4/1972    Price et al. ............... 264/13

(Continued)

FOREIGN PATENT DOCUMENTS

EP    0 145 197    9/1989

OTHER PUBLICATIONS

Nebe-von Caron G et al (1998) Assessment of bacterial viability status by flow cytometry and single cell sorting. J Appl Microbiol, vol. 84, pp. 988-998.*

(Continued)

*Primary Examiner*—Jon Weber
*Assistant Examiner*—Clark D. Petersen
(74) *Attorney, Agent, or Firm*—Cooley Goodward Kronish LLP

(57) ABSTRACT

A method for forming a substantially solid product containing a desired quantum of bioparticle, the method comprising (a) providing a sample of bioparticle in liquid form; (b) selecting a desired quantum of the bioparticle; and (c) forming a substantially solid product containing the desired quantum of the bioparticle, wherein the product is capable of being transferred between containers in its solid form without loss of bioparticle, and wherein the product is capable of releasing the bioparticle in a liquid.

10 Claims, 1 Drawing Sheet

U.S. PATENT DOCUMENTS

Figure 1:
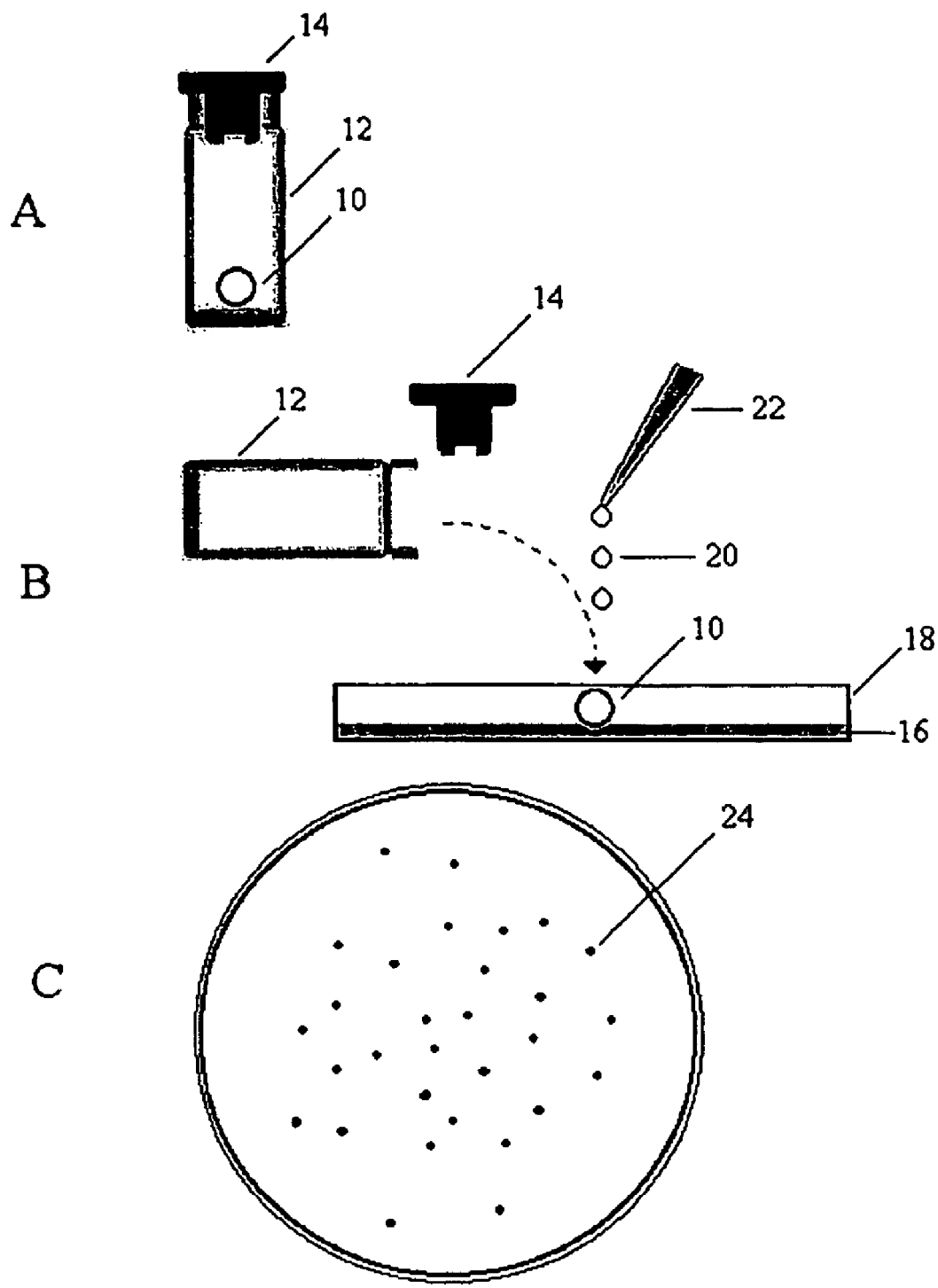

| | | | |
|---|---|---|---|
| 3,932,943 A | 1/1976 | Briggs et al. | 34/5 |
| 4,243,687 A | 1/1981 | Kline | 426/62 |
| 6,106,836 A | 8/2000 | Wilderbeek et al. | 424/184.1 |
| 6,780,581 B2 * | 8/2004 | Vesey et al. | 435/5 |

OTHER PUBLICATIONS

Leslie SB et al (Oct. 1995) Trehalose and sucrose protect both membranes and proteins in intact bacteria during drying. Appl Environ Microbiol, vol. 61, No. 10, pp. 3592-3597.*

Van Noorden, 1991, *Histochemical Journal*, 23, 429-435.
Champagne et al., 2000, *Journal of Applied Microbiology*, 88, 124-131.
Peterz et al., 1993, *Journal of Applied Bacteriology*, 74, 143-148.
Malucelli et al., 1995, *Vaccine*, 13, 3, 273-275.
Pembrey et al., 1999, *Applied and Environmental Microbiology*, 65, 7, 2877-2894.
Meno et al., 1998, *Arch Microbiol*, 170, 339-344.
Kairo et al., 1999, *Vaccine*, 17, 2423-2428.

* cited by examiner

PRODUCTS CONTAINING QUANTUM OF BIOPARTICLES AND METHOD FOR PRODUCTION THEREOF

CROSS REFERENCE TO RELATED APPLICATIONS

This application is a 371 filing of PCT/AU02/01216 filed Sep. 4, 2002, which claims priority to Australian Patent Application No. PR 7505, filed Sep. 5, 2001. This application is also a Continuation-in-Part of application Ser. No. 09/949,860, filed Sep. 12, 2001, now U.S. Pat. No. 6,780,581 granted on Aug. 24, 2004. Each of these applications are herein incorporated by reference in their entireties.

TECHNICAL FIELD

The present invention relates to products containing a quantum of bioparticles, particularly a quantum of microorganisms suitable for use in tests and assays.

BACKGROUND

There are many procedures performed in life sciences that involve the manipulation of small bioparticles such as cells, bacteria, viruses, protozoa, sperm, eggs, embryos and larvae. Generally the manipulation of these small bioparticles is inherently difficult because the bioparticles are too small to be visualised with the naked eye.

Where one is performing an experiment or procedure that involves adding bioparticles to a vessel (for example, a test tube) there is currently no simple technology available which allows one to know exactly, or at least with a minimal degree of error, how many bioparticles have been added. Typically one would prepare a suspension of the bioparticles and then perform an analysis (for example, enumeration by microscopy or culture on an agar plate), to estimate the number of bioparticles per volume of liquid. An aliquot of this suspension, containing an estimated number of bioparticles, would then be used for a desired purpose; the exact number of bioparticles in the aliquot not being known.

In addition to problems associated with estimation of the numbers of bioparticles by sampling, further problems may result during manipulation of the bioparticles in a particular procedure. For example, an unknown amount of the bioparticles are inevitably lost due to factors such as adhesion to surfaces of vessels or pipettes used, or to denaturation or death of some of the bioparticles. Further, bioparticles can lose their viability or contents over time and accordingly products containing such materials may suffer from a short shelf life. Combined with the above problems, these factors may create gross inaccuracies in experimental data.

A number of products are known which attempt to provide a standardised product having a defined number of bioparticles. However, these products unfortunately fail to address all of the problems above mentioned, and accordingly, may be considered to fall short of providing a desirable product. For example, the degree of error in respect of the number of bioparticles present from one sample of a product to another sample of the same product is likely to be in the order of greater than 50%, in many cases the number of bioparticles present may vary 10 to 100 fold or more.

One example of such known products is Cultiloops® (Oxoid, Australia). Cultiloops® are disposable bacteriological culture loops that contain a loopful of freeze-dried culture of a specific microorganism and are generally used for quality control purposes in microbiology laboratories. While Cultiloops® save time in the preparation of cultures for quality control they unfortunately do not contain accurately defined numbers of cells per loopful. Further, it is possible that a number of the cells present may not be in a viable state.

Several companies supply vials containing an approximate number of microorganisms in a freeze-dried form. Typically, these are manufactured to an accuracy of 1 order of magnitude; for example, a vial will contain between 1000 and 10000 bacteria. To use these products, one generally adds water to the vial to resuspend the freeze-dried microorganisms, subsequently using a pipette to transfer the microorganisms to a sample. Due to the nature of this product, and the means by which it is used, it may not be considered to adequately address the issue of providing accurate and consistent numbers of bacteria, or the issue of the loss of unknown quantities of bacteria during manipulation as a result of adhesion to the side of the vial or the pipette.

BTF Pty Ltd (Australia) markets a product known as EasySeed™ C&G that provides an accurately defined number of inactivated *Cryptosporidium* and *Giardia* in liquid in a test tube. While it may be considered that this product overcomes many of the issues associated with providing accurate numbers of microorganisms, during use of the product, an unknown number of the *Cryptosporidium* and *Giardia* are generally lost due to adhesion to the side of the test tube or pipette. Further, the cells are not provided in a viable state.

A further example of a presently available product are lenticles, freeze-dried quality control samples prepared by the UK Public Health Laboratory Service (PHLS). Lenticles are prepared by pipetting drops of a viscous bacterial culture a surface and drying the drops to form a lens-shaped freeze-dried pellet. While the lenticules may be considered to overcome the inaccuracies associated with handling liquid quality control samples, they unfortunately do not contain accurately defined numbers of bacteria.

A further product, known as TrueCount® (Becton Dickinson, San Jose, USA), is used in conjunction with flow cytometry to allow one to determine the number of specific cells per millilitre of blood, for example. The product consists of dried balls of approximately 1 mm diameter that contain approximately 50,000 fluorescent beads of approximately 5 µm diameter. While this product may overcome problems associated with the loss of materials during manipulation of a liquid sample, it does not contain an accurately defined number of beads within the dried ball. Further, as the beads do not represent biological-derived material, the product, and the procedure of producing the product, is not concerned with, and therefor may not adequately address, the issue of accuracy or maintenance of viability of the materials.

U.S. Pat. No. 3,932,943 describes a process for the production of a homogeneous, lyophilised product containing at least one biologically active component. The process involves spraying a solution or colloidal suspension containing the biologically active component into a moving bath of fluorocarbon refrigerant, and subsequently lyophilising the resultant frozen droplets. The inventors report that the product has a spherical shape, free-flowing properties, and rapid dissolution times. However, the process does not address the issue of preparing a product that contains accurately defined numbers of bioparticles. In addition, it may be considered that this process does not adequately address the issue of maintenance of bioparticle viability, especially where such bioparticle is a cell.

U.S. Pat. No. 6,106,836 describes a process for the production of a vaccine product comprising a container with freeze-dried vaccine components therein. The process involves the formation of balls containing biological components of estimated numbers utilising the steps of freezing droplets of a suspension containing the biological components in a cryogenic liquid and subjecting them to freeze-drying. The process of this patent does not immediately address the issue of preparing a freeze-dried product that contains accurate numbers of bioparticles. By contrast, products containing estimated numbers of components are made via the above mentioned process, their titre measured, and then a number of products combined, or used to supplement another product, to obtain a desired quantity of components. In addition, the process of U.S. Pat. No. 6,106,836 may not be considered to adequately address the issue of maintenance of the viability of bioparticles during processing. Rather, the process centres on the loss of viability of the bioparticles followed by supplementation of the resultant product with additional viable materials.

Further, U.S. Pat. No. 3,655,838 describes a method for the preparation of pelletised reagents purportedly in a stable, accurate form. In this method, a suspension containing predetermined concentrations of desired reagents is formed into calibrated droplets which are allowed to fall into a liquid having certain characteristics, one of which is a temperature gradient suitable to freeze the droplets. Subsequently, the droplets are dried to form the pelletised product. While the method aims to provide products containing predetermined and pre-tested measured amounts of certain reagents, it may be considered to suffer from inaccuracies in the actual concentration or number of specific components present, due to methods employed to arrive at initial concentration values. Further, the method may be considered not to accurately address the issue of maintenance of viability where the reagent to be processed is a bioparticle.

Current methods for preparing DNA and protein standards for example, typically rely on measuring the absorbance of a solution of DNA or protein and calculating the concentration and then diluting the solution to the desired concentration. These methods do not provide accurate standards.

The present inventors have now developed methods which are capable of producing a desired quanta of bioparticles in products suitable for use as accurate standards for a variety of biological and analytical applications.

SUMMARY OF INVENTION

The present inventors have devised processes which surprisingly allow for the preparation of a substantially solid product containing a desired small quantum or number of microorganisms in a stable format that can be easily manipulated while minimising the loss of any of the microorganisms. The process is particularly applicable to the formation of a product comprising an accurate small number of viable or stable microorganisms. It is believed that the nature of the product according to the invention will allow for simplified manipulation of microorganisms and for more accurate and reproducible results from procedures utilising the microorganisms.

In a first aspect, the present invention provides a process for forming a product containing a desired number of microorganisms, the method comprising:
(a) providing microorganisms; (b) selecting a desired number of the microorganisms using means to sense a bioparticle; and (c) forming a substantially solid product containing the desired number of microorganisms, wherein the product is capable of being transferred between containers in its solid form without loss of any microorganism, and wherein the product is capable of releasing the microorganism in a liquid.

In a second aspect, the present invention provides a process for forming a product containing a defined number of microorganisms, the process comprising:
(a) providing microorganisms selected from the group consisting of microorganisms, cells, vectors, particles containing a biological material, and mixtures thereof in suspension; (b) selecting a defined number of the microorganisms of between 1 and 1000 from the suspension by means to sense a microorganism; (c) capturing the defined number of microorganisms in a frozen body; and (d) drying the frozen body to produce a product containing the defined number of microorganisms, wherein the product is capable of being transferred between containers in its solid form without substantial loss of the microorganisms, wherein the product is capable of releasing the microorganisms in a liquid, and wherein the defined number of the microorganisms in the product when measured in two or more replicates is within a standard deviation of less than about 10% of the defined number.

In a third aspect, the present invention provides a substantially solid product containing a desired number of microorganisms of between 1 and 1000, wherein the product is capable of being transferred between containers in its solid form without loss of any microorganism, and wherein, the product is capable of releasing the quantum of microorganism in a liquid.

In a fourth aspect, the present invention provides a product containing a quantum of microorganism produced by the process according to the first or second aspects of the present invention.

In a fifth aspect, the present invention provides use of a product containing a quantum of microorganism according to the third or fourth aspects of the present invention in an assay or test.

In a sixth aspect, the present invention provides use of a product containing a quantum of microorganism according to the fifth aspect of the present invention in an assay or test.

In a preferred form, the microorganism is selected from bacteria, cells, vectors, particles containing a biological material, and mixtures thereof. The microorganisms can be viruses, bacteria, yeast, fungi, parasites or protozoa, the cells can be plant cells, animal cells, or gametes, the vectors can be plasmids or viroids, and the particles can be beads, for example that contain protein, peptides, polysaccharides, nucleic acid or mixtures thereof bound to the surface of the particle for example.

Preferably, the microorganisms are selected from the group consisting of *Legionella, Salmonella, Leptospirosis, Escherichia, Saccharomyces, Clostridium, Vibrio, Pseudomonas, Bacillus, Streptomyces, Staphylococcus, Enterobacter, Listeria, Candida, Zygosaccharomyces*, and mixtures thereof. More preferably, the bacteria are *Escherichia coli* or *Bacillus cereus*.

Preferably, the parasites are selected from *Cryptosporidium, Giardia, Cyclospora, Toxoplasma, Eimeria* and mixtures thereof.

The bioparticle may also be in the form of particle containing or having biologically derived material such as protein, peptide, carbohydrate, polysaccharide, peptide, nucleic acid or mixtures thereof.

Further examples of bioparticles are blood cells, human imunodeficiency virus (HIV), Norwalk virus, herpes simplex virus.

A product according to the invention may comprise a single species of bioparticle, or alternatively, two or more species of bioparticle.

When the bioparticle is a living organism, the product preferably contains a quantum of viable organisms. In this form, the product is particularly suitable for use as a quality control in microbial cultures. It will be appreciated, however, that there are other situations where viability is not necessary for the product. For example, the product may include a quantum of proteins or nucleic acids which are useful for biochemical or molecular biology standards. The protein may be an enzyme which is required at a desired amount for an assay. Similarly, the nucleic acid may be a quantum of a gene or nucleic acid probe which can be used as a molecular biological tool in an assay.

In a preferred form, the sample of bioparticle is in liquid form. Examples include but not limited to microbial cultures, suspensions of cells, suspensions of particles including one or more bioparticles. The present inventors have found that a flow cytometer is particularly suitable for selecting and capturing a quantum of the bioparticle in liquid form. In addition, the selecting and capturing a quantum of the bioparticle in liquid form can be carried out using any accurate measuring device. Examples include pipettes, micro-pipettes and other micro-metering devices. Importantly, the device or step should not retain or adversely affect the capture of the desired quantum of bioparticle.

In a preferred form, the quantum of bioparticle is selected by accurately counting a desired number of bioparticle units and capturing the desired number in a defined volume. The defined volume is usually less than about 1 ml, usually less than 0.1 ml, and typically about 0.03 ml.

Preferably, a solid body is formed by freezing, preferably snap-freezing a volume of liquid containing the quantum of bioparticle and then drying the frozen body to form the product. One preferred form is carried out by placing the defined volume, usually a droplet, into a cryogenic liquid. The cryogenic liquid can be liquid nitrogen, liquid helium or liquid oxygen. More preferably, the cryogenic liquid is liquid nitrogen. The frozen liquid is then preferably processed by freeze-drying to form a substantially solid product, usually as a small roundish mass in the form of a ball or a pellet.

In another preferred form, the product is produced without freezing. For example, a drop or aliquot containing the bioparticle could be dropped or placed onto a surface and then dried. In one form, the material could be placed on an absorbent material and then dried.

In one preferred form, the cryogenic liquid is placed in a container and a droplet is placed in the container to form a frozen body. The container holding the frozen body is then subjected to freeze drying to form a substantially dry solid product within the container. After drying, the container can be capped or sealed for storage and transport of the product. To provide an environment that will maintain the stability of bioparticle if required, the container can be capped or sealed whilst under vacuum or it can be filled with an inert gas. In this form, the quantum of bioparticle is captured within the dry solid product which can be free to move within the container. The product can be manipulated in its dry state without loss of any bioparticle to the container or its surroundings.

Another advantage of the present invention is that the desired quantum of bioparticle can be accurately dispensed. When measured in two or more replicates, the number of the bioparticle in the product is within a standard deviation of less than about 20%, preferably less than about 15%, more preferably less than 10%, and even more preferably less than or around 5%. The method according to the present invention is capable of consistently providing a number of products having a quantum of bioparticle with an accuracy of between about 4% and 8%.

The present invention is suitable for producing a large number of products having the same desired quantum of bioparticles. The method is suitable for automation to produce large numbers of products in a batch, for example.

The method according to the present invention is suitable for providing small numbers of bioparticle of less than about $10^5$. The method according to the present invention is particularly suitable for providing small numbers of bioparticle of less than about $10^4$, preferably less than about $10^3$. In particular, the method can accurately provide numbers of bioparticle of less than about 100. This achievement is quite remarkable when considering that the bioparticle can be cells or microorganisms in relatively large volumes compared to the actual size of the bioparticle.

In one preferred form, the method further includes the step of selecting a desired bioparticle type from a mixture of different bioparticles. The selection may be on any suitable physical characteristic of a bioparticle in solution. Examples include, but not limited to size, shape, colour, fluorescence, viability, electrorotation, impedence, refractivity, light scattering, time of flight through a laser beam, mass or charge. Characteristics can also be measured by reacting the bioparticles with a molecule that responds to certain properties within the bioparticle. For example, a fluorogenic substrate such as fluoresein diacetate that becomes fluorescent in the presence of esterase activity within the cell. Other examples include, but not limited to nucleic acid stains such as propidium iodide and syto 16, the cell respiration stain 5-cyano-2,3-ditolyl tetrazolium chloride (CTC), enzymatic substrates, lectins, antibodies, DNA probes.

Preferably, one freeze-dried product is formed per quantum of desired bioparticles to form the product. Alternatively, two or more freeze-dried products are formed per quantum of desired bioparticles to form the product.

Preferably, the method further comprises a final quality control step. Preferably, the quality control step involves one or more of:

counting the number of bioparticles contained within one or more products; and measurement of the uniformity of the product, by weighing or measuring the size of one or more products.

Preferably, the quantum of bioparticles comprises a single species or type of bioparticle. Alternatively, the quantum of bioparticles comprises a mixture of two or more species or types of bioparticle.

Each product may additionally comprise supplementary agents. In one form, the supplementary agents are those which aid in maintaining viability or stability of the bioparticle. More preferably, the supplementary agents are cryopreservatives.

Other suitable supplementary agents include, but not limited to one or more of sucrose, trehalose, lactose, maltose, glucose, galactose, raffinose, fructose, xylose, cellobiose, gelatin, xantham gum, guar gum, maltodextrans, polyethylene glycol, dextran, polyvinyl pyrrolidone, sodium thiosulfate, activated charcoal, ascorbic acid, ascorbate peroxidase, glutathione reductase, peroxiredoxin, sodium glutamate, proline, potassium glutamate, proline betaine, glycine betaine, skim milk, serum, trypsin, peptone, tryptone, yeast extract, soy protein, meat extract, mannitol, glycerol, sorbitol, inositol, butanol, tertiary butyl alcohol, honey, sodium acetate, myo-inositol, calcium chloride, whey, hydroxyectoine, and ectoine.

In one preferred embodiment, the present invention provides a method for forming a product containing a desired quantum of viable bacteria, the method comprising:
(a) providing a sample of bacteria in liquid form;
(b) selecting a quantum of the bacteria in a defined volume using a cytometer;
(c) adding the defined volume of the bacteria as a drop to a cryogenic fluid to form a frozen ball containing the quantum of the bacteria; and
(d) subjecting the frozen ball to freeze-drying to form a substantially dry solid product containing the quantum of the bacteria, wherein the product is capable of being transferred between containers in its solid form without loss of the bacteria, and wherein the product is capable of releasing the quantum of viable bacteria in a liquid.

Preferably, the bacteria are selected from the group consisting of *Legionella, Salmonella, Leptospirosis, Escherichia, Saccharomyces, Clostridium, Vibrio, Pseudomonas, Bacillus, Streptomyces, Staphylococcus, Enterobacter, Listeria*, and mixtures thereof. More preferably, the bacteria are *Escherichia coli* or *Bacillus cereus*. The microorganism may also be a yeast such as *Candida* and *Zygosaccharomyces*.

In another preferred embodiment, the present invention provides a method for forming a product containing a quantum of a protein, carbohydrate, polysaccharide, gene or a nucleic acid molecule, the method comprising:

(a) providing a sample of a bioparticle containing a known number of copies of a protein, carbohydrate, polysaccharide, gene or nucleic acid molecule in liquid form;
(b) selecting a quantum of the bioparticle in a defined volume using a cytometer;
(c) adding the defined volume of the bioparticle as a drop to a cryogenic fluid to form a frozen ball containing the quantum of the bioparticle; and
(d) subjecting the frozen ball to freeze-drying to form a substantially dry solid product containing the quantum of the bioparticle, wherein the product is capable of being transferred between containers in its solid form without substantial loss of the bioparticle, and wherein the product is capable of releasing the quantum of the bioparticle containing the quantum of the a protein, carbohydrate, polysaccharide, gene or a nucleic acid molecule in a liquid.

Preferably, the bioparticle is selected from microorganism, cell or particle containing the protein, carbohydrate, polysaccharide, gene or nucleic acid molecule.

For example, a gene of interest together with a reporter gene having a detectable gene product can be added to a bacterium under the control of the same promoter. Only bacteria that produce the detectable reporter gene product can be selected which would express a defined level of both genes. Thus a defined amount of the gene of interest would be produced in the product.

Preferably the bioparticle is microorganism containing a gene or nucleic acid molecule.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred forms will be described with reference to the following drawings and examples.

BRIEF DESCRIPTION OF THE DRAWINGS

FIG. 1A is a schematic diagram of a product according to the present invention in the form of a substantially solid freeze-dried ball containing a known number of bacteria which has been provided in a stoppered vial;

FIG. 1B is a schematic diagram showing use of the substantially solid freeze-dried ball shown in FIG. 1A being removed from the vial and placed on the surface of a petri dish containing bacterial culture media; and FIG. 1C is a schematic diagram showing bacterial colonies formed on the surface of the culture media in the petri dish after growth of the bacteria from the substantially solid freeze-dried ball after addition of a suitable liquid to disperse the bacteria.

MODE(S) FOR CARRYING OUT THE INVENTION

The invention relates to a process for preparing a product which contains a desired quantum of bioparticle. The product of the invention generally comes in the form of a single mass, preferably in the form of a ball or pellet. However, the inventors contemplate the product also comprising a number of balls or pellets, preferably 3 to 10 balls or pellets, which taken together provide the quantum of the bioparticle. While the following description focuses on the embodiment of the invention in which the product represents a single ball, it will be appreciated by skilled persons in the art that the description may be readily read to encompass the embodiment in which the product comprises a group of balls, or any other forms of a substantially solid mass.

In order to facilitate manipulation of the product following formation thereof, the ball is preferably large enough to be visible to the human eye. Accordingly, the product of the invention is preferably about 0.1 to 10 mm in diameter or width, and more preferably about 4 mm. However, it will be appreciated that the product may have a diameter or cross-sectional width larger than 10 mm, or of a diameter or cross-sectional width smaller than 0.1 mm.

As used herein, the term "bioparticles" refers to particles of a biological nature. Such bioparticles may preferably be cells, of prokaryotic or eukaryotic origin, or alternatively, proteins or cell organelles such as nuclei, viruses, viroids, plasmids, or vectors containing known nucleic acid material. Accordingly, bioparticles which may be applicable to the invention include, bacteria, fungi, parasites, yeast or virus, single or multi-cellular protozoa, or prions. Examples of such bioparticles include *Legionella, Salmonella, Leptospirosis, Escherichia, Saccharomyces, Clostridium, Vibrio, Pseudomonas, Bacillus, Streptomyces, Staphylococcus, Enterobacter, Listeria, Candida, Zygosaccharomyces, Cryptosporidium, Giardia, Cyclospora, Toxoplasma, Eimeria*, blood cells, HIV, Norwalk virus, herpes simplex virus. The bioparticle may also be in the form of particle containing or having biologically derived material such as protein, peptide, carbohydrate, polysaccharide, peptide, nucleic acid or mixtures thereof. A product according to the invention may comprise a single species of bioparticle, or alternatively, two or more species of bioparticle.

As previously mentioned, the invention is particularly applicable to the formation of a product comprising viable bioparticles. As used herein "viable bioparticles" are materials capable of working, functioning, or developing substantially as in their native state, or a state to which they have been designed to have via laboratory manipulation. Accordingly, in the case of cells, "viable bioparticles" are those materials capable of, for example, functioning, growing, developing and, where applicable, infecting a host.

As used herein a "quantum" of bioparticles refers to the number of bioparticles present, or desired to be present, within the product of the invention. A "quantum" does not necessarily imply that exact numbers of bioparticles will be present within a sample or product according to the invention without some small degree of variation. Typically, when measured in two or more replicates, the number of the bioparticles in the product is within a standard deviation of less than about 20%, more preferably less than about 10%. In practice, the present invention can deliver a quantum of bioparticle in a product with an accuracy not previously achieved consistently by other methods. For example, small numbers of less than about 100 bioparticles can readily be provided with an accuracy of less than about 7% standard deviation. Generally, "quantum" of bioparticles, refers to the number of bioparticles estimated to be present via conventional means used in the art; for example, enumeration by microscopy or culture.

According to the invention, a "quantum" of bioparticles, is the number of bioparticles present in the product of the invention. Preferably, a "quantum" represents an exact number of bioparticles. However, the inventors contemplate a minimal degree of error in the number of bioparticles. The inventors believe such error may be monitored and minimised by conducting quality control checks of the products formed in the method of the invention.

It will be appreciated that the number of bioparticles selected to be present within the product of the invention may vary depending on the nature of the bioparticles to be processed, the desired size of the final product (the freeze-dried balls for example), and the ultimate use to which the final product will be put. For example, a product containing *Escherichia coli*, which is desired to be used in quality control of microbiology culture media, will preferably contain a small number, typically 30 viable *E. coli* cells. In addition, a product according to the invention may comprise a single species of bioparticle, or alternatively, a mixture of two or more specific species or types of bioparticles.

The product of the present invention preferably contains constituents in addition to the quantum of bioparticles. For microorganisms, the "constituents" will generally comprise those components of culture media in which the microorganisms were grown or suspended in prior to processing according to the invention. Such constituents will be readily recognised by persons of general skill in the field, and will become further apparent from the description of the method of the invention to follow. The product of the invention may additionally contain supplementary agents which may have been introduced during one or more steps of the process, or added to the growth or suspension media in which the microorganisms were initially prepared.

"Supplementary agents" are those agents which may aid in the preservation of the viability or stability of the bioparticles during processing (for example, cryopreservatives such as glycerol or dimethyl sulfoxide (DMSO), antioxidants such as activated charcoal, sugars such as glucose). Alternatively, agents which may be desired to be present in the final product based on a particular application to which it will be put. For example, a dye may be added so that when, in use, the product is added to a liquid sample, a colour change of the sample will occur. Similarly, a detergent may be added to assist with re-hydration, or common bulking agents may be used to help give body to the resultant products of the invention. Such agents may be introduced at various stages during the method of the invention. It is preferable, however that at least some agents be added at the initial stage of preparing the bioparticles.

The inventors particularly contemplate the presence of cryopreservative agents within the product of the invention. Such appropriate cryopreservative agents, which are well known in the art, include glycerol, sugars which may be used at a concentration of between about 1 and 20% (w/v), or dimethyl sulfoxide (DMSO), which may be used at a concentration of between about 1 and 20% (v/v).

The inventors also contemplate the presence, within the products of the invention, of protective agents that assist the survival or maintenance of the viability or stability of the bioparticles during the drying process. Such appropriate protective agents include, but not limited to, activated charcoal, honey, sodium glutamate, raffinose and animal serum. Skilled persons may be able to identify further appropriate protective agents. These protective agents may be used at concentrations of between about 1 and 30% (v/v), for example.

It will be appreciated that the cryopreservative and the protective agents used in the invention may be varied so as to obtain the most optimal conditions for the particular bioparticle to be processed. By way of example, where the bioparticles represent bacteria such as *E. coli*, appropriate cryopreservatives include glycerol and DMSO and appropriate protective agents include activated charcoal.

An example of a product according to the present invention in the form of a ball and its use is shown in FIGS. 1A to 1C. In this embodiment, the solid product is in the form of a substantially solid freeze-dried ball 10 provided in a vial 12 (FIG. 1A). The vial 12 is sealed with a stopper 14 for convenient storage and transport. It will be appreciated that other forms of storage would also be suitable for the solid product. The ball 10 in its solid form is transferable from the vial 12 to another container without the concern of any loss of the bioparticle from the ball 10. As the bioparticle is contained in or associated with the ball, portions of the bioparticle cannot be left in a container when transferred to some other container.

FIG. 1B shows an example of dispensing the ball 10 from the vial 12 to a solid microbial culture medium 16 in a petri dish 18 for subsequent culture of the bioparticle in the form of a microorganism. The stopper 14 is removed from the vial 12 and the ball 10 is tipped onto the surface of the culture medium 16. When the ball 10 is removed from the vial 12, there will be no microorganism or other bioparticle present or left over in the vial 12. The microorganisms in the ball 10 can then be obtained by adding any suitable liquid. In FIG. 1B, liquid in the form of drops of sterile water 20 are added to the ball 10 on the medium 16 using a pipette 22. The ball 10 then dissolves releasing the microorganisms onto the medium 16. The petri dish 18 can then be incubated at a desired temperature for a period of time for the microorganisms to grow. Each microorganism will grow forming discrete colonies 24 on the medium 16 as indicated in FIG. 1C.

Methods

A preferred embodiment of the invention is described in terms of the formation of a product in the form of a single ball comprising a quantum of one species of bioparticle in the form of a microorganism. It should be appreciated however, that the embodiment is readily applicable to a product comprising a group of balls or other solid forms, which taken together provide the quantum of the same or different type of bioparticle.

In general terms, a preferred method for forming freeze-dried balls of the invention comprises the following steps (a) providing a sample of bioparticle in liquid form;

(b) selecting a quantum of the bioparticle in a defined volume;

(c) freezing the defined volume of liquid to form a frozen ball containing the quantum of the bioparticle;

(d) drying the frozen ball to form a substantially dry solid product in the form of a freeze-dried ball containing the quantum of the bioparticle, wherein the ball is capable of being transferred between containers in its solid form without loss of any bioparticle, and wherein the ball is capable of releasing the bioparticle in a liquid; and optionally (e) carrying out one or more quality control steps on the freeze-dried product.

Each step of the preferred process will be described more fully below.

Providing a Sample of Bioparticle in Liquid Form

The first step of the method of the invention involves preparing and providing a sample of bioparticle in a liquid suspension media.

Generally, the bioparticle will be prepared according to methodology well known in the technical field to which the invention relates. For example, in the case of prokaryotic or eukaryotic cells, the cells may be grown in an appropriate liquid growth media (for example, nutrient broth (Oxoid, Australia) in the case of *E. coli*) to a desired density. In any case, it will be appreciated that standard texts referred to in the art will provide information of appropriate means for providing various bioparticles of use in the invention.

As will be appreciated, the liquid growth media referred to above will vary depending on the nature of the bioparticle to be processed; and the ultimate use to which the product of the invention will be put. For example, where the bioparticle represents cells, the media in which they have been grown may represent the suspension media. Alternatively, in the case of cells, they may be harvested from growth media and resuspended in an alternative media, which may be more suitable, having regard to the use to which the final product will be put. In any case, those persons of skill in the art may readily be able to identify suitable suspension media for a particular bioparticle based on well-known principles in the art and by reference to standard texts.

The preparation of a bioparticle in the form of a microorganism for subsequent culturing or growth should preferably aim to maximise maintenance of viability or stability of the microorganism throughout the subsequent manufacturing process. Skilled persons will be able to recognise such conditions. However, by way of general example, the optimisation of conditions at this stage of the manufacturing process may involve growth of the microorganism under specific conditions that enhance robustness. For example, growth of the microorganism to a particular stage of growth known, or found, to be optimal for survival of a particular microorganism. Alternatively, exposure of the microorganism to conditions such as starvation or heat shock may be advisable. By way of specific example, *E. coli* cells that are in the stationary growth phase will maintain their viability better than cells in logarithmic growth phase. Bacteria such as *Legionella* may better maintain viability through the manufacturing process if they have been starved for several days by storage in distilled water. There are many other situations or conditions for other microorganisms well known to the art that would also be applicable for the present invention.

The inventors contemplate that maintenance of the viability of the microorganisms during subsequent processing in the invention, may be enhanced by introducing supplementary agents to the growth and/or suspension media within which the microorganisms may be grown and/or suspended. The addition of supplementary agents to the growth and/or suspension media for alternative reasons is also contemplated by the inventors. Suitable supplementary agents are described above.

In addition, the inventors contemplate that the microorganisms may be modified during the initial preparation step. Such modification may, for example, enhance subsequent analysis and sorting or alternatively, may provide desirable characteristics suited to the ultimate use to which the product of the invention will be put. For example, cells may be in recombinant form, or may be labelled or tagged with suitable agents (for example, antibodies, fluorescent stains such as fluorescein diacetate (FDA), propidium iodide (PI), oligonucleotides).

Selecting a Quantum of the Bioparticle in a Defined Volume

The second step of the manufacturing process of this preferred embodiment of the invention involves manipulating the liquid sample containing the bioparticles using flow cytometry techniques known in the art (Shapiro, H. M. (1990) Flow Cytometry in laboratory microbiology: new directions. *American Society for Microbiology News* 56, 584-588; Shapiro, H. M. (1995) A practical guide to flow cytometry, third edition. A. R. Liss, New York). By using such technology, desired bioparticles may be identified and selected. Such "desired bioparticles" are materials of a desired nature or character. For example, a particular cell type which may be present in a background of alternative bioparticles, or those cells of a certain type which are viable.

As will be appreciated, the technique of flow cytometry may be used to analyse and select bioparticles based on preselected physical characteristics. For example, absorption at a particular wavelength, density, magnetism, specific gravity, impedance, ability to scatter light, luminescence, or fluorescence. In addition, the inventors contemplate the use of Coulter sensing and raman microscopy in conjunction with flow cytometry to analyse and sort bioparticles according to the invention.

While a single specific preselected characteristic of a particular bioparticle may be used for analysis or selection thereof in this step of the manufacturing procedure of the invention, the inventors also contemplate the use of any other suitable method or device for selecting a number of bioparticles from a liquid sample. Examples include pipette, micro-pipette, metering devices and multiparameter flow cytometry. "Multiparameter flow cytometry" is used herein to mean the measurement of several characteristics of a particular bioparticle to differentiate it from another.

The techniques available to select bioparticles using flow cytometry are well documented in the art. However, by way of exemplification, where one wishes to rely on optical analysis, a sample containing bioparticles may be mixed with one or more dyes, fluorescent or luminescent agents, or antibodies conjugated to such agents prior to analysis via flow cytometry so that specific bioparticles are stained or tagged. An example of such a process involves the use of the dye fluorescein diacetate which specifically stains viable cells. Following staining with fluorescein diacetate, the sample may be analysed and single viable bioparticles that are at a specific stage of their life cycle identified.

The desired bioparticles may be selected, or sorted, from the sample, on the basis of the preselected characteristics mentioned herein before, and in accordance with flow cytometry technology. Utilising the flow cytometer, a quantum of a desired material, or materials, may be sorted or captured.

In accordance with this step of the manufacturing process, the flow cytometry apparatus may express a volume of liquid containing the quantum. Preferably, the apparatus is configured such that the liquid containing a quantum of the bioparticles is forced through an orifice in a downward direction so that a droplet is formed. The size of the orifice can be changed to precisely control the volume of the droplet.

While the above technique is considered by the inventors to be a preferred means for material sorting and formation of a volume of liquid comprising a quantum of selected bioparticles, it is contemplated that alternative means known in the art may be used. For example, the invention may employ piezo capillary dispensing, a piezo-actuated catcher tube, charged droplet deflection, acoustic manipulation (Standing Wave, Shock Wave), electrostatic manipulation, optical tweezers, pipettes, micro-pipettes or other metering devices. Those of general skill in the art may realise further techniques may be readily applicable to the present invention.

The inventors contemplate the fluid output from the cytometer being mixed with supplementary agents prior to forming the droplets into a cryogenic liquid. Some supplementary agents may interfere with the analysis and sorting of the bioparticles if they are added into the flow cytometer sheath fluid. For example, activated charcoal and dyes such as malachite green may interfere with cytometric analysis. By introducing supplementary agents at this stage of the procedure after counting, this problem may be overcome.

Freezing the Defined Volume of Liquid to Form a Frozen Ball Containing the Quantum of the Bioparticle In this step of the process, the droplets formed in the second step above are dropped into a vessel that contains a cryogenic liquid, preferably liquid nitrogen, resulting in the formation of frozen balls that contain a desired quantum of selected bioparticle.

This freezing step is preferably performed at a temperature that is optimal for the preservation of the viability or stability of the bioparticles. It will be appreciated that the optimal temperature may vary depending on the nature of the bioparticles being prepared. However, those of general skill in the art will readily be able to determine the optimum temperature range by performing experiments at a range of different temperatures and comparing the numbers of bioparticles that survive the freezing process. Accordingly, while the use of liquid nitrogen is preferred, it will be appreciated that a number of alternative cryogenic liquids may be employed in the invention in order to satisfy a particular temperature requirement. For example, liquid helium and liquid oxygen are suitable options. Persons skilled in the field of technology to which the invention relates will readily be able to identify the most appropriate cryogenic liquid to be used based on the temperature requirements of a particular bioparticle. In addition, the temperature of the cryogenic fluid could be controlled by adjusting the pressure of the cryogenic fluid in its holding vessel.

Drying the Frozen Ball to Form Forming a Substantially Dry Solid Product

In accordance with the present invention, the frozen balls formed in the third step above are then freeze-dried. Freeze-drying may be conducted according to standard procedures; (Oetjen, Georg-Wilhelm. *Freeze-drying*. Wiley-VCH, Weinheim (1999); Rowe, Terence W. G. Edwards freeze-drying handbook. Edwards High Vacuum, Crawley (1978); Mellor, J. D. Fundamentals of freeze-drying. Academic Press, London (1978).

As it will be appreciated, it is desirable that this step be conducted in a manner which maintains the viability or stability of the bioparticles. Of course, such conditions may vary depending on the nature of the bioparticles being prepared. However, a person of general skill in the art will readily be able to determine the most effective conditions based on the teachings of Oetjen (1999), Rowe, Terence W. G. Edwards freeze-drying handbook. Edwards High Vacuum, Crawley (1978), and Mellor, J. D. Fundamentals of freeze-drying. Academic Press, London (1978).

Optional Quality Control

The inventors contemplate the optional use of a quality control (QC) step following the formation of the product as above described. Such QC may allow for the minimisation of error in the number of bioparticles present within the balls and/or the size of the products produced. QC may involve either counting the number of bioparticles contained within selected samples of the product by analytical methods such as culturing the bioparticles on agar plates, or by flow cytometry, or by nucleic acid-based analytical methods such as the polymerase chain reaction (PCR) within selected samples of the product, or measurement of the uniformity of the product, for example by weighing or measuring the size of selected balls.

Following formation of the product in accordance with the invention, the balls may be packaged and stored in a test tube, vial or similar container. Alternatively, the balls can be packaged in blister packs similar to those used for tablets. The balls are preferably stored under conditions that minimise the exposure of the balls to oxygen and humidity. Suitable storage conditions include, for example, storage under vacuum or storage under inert gasses such as nitrogen or argon. Alternatively, a dehumidifying agent such as silica gel can be packaged with the balls. The balls can be packaged individually or in groups. For example, a ball that contains 10 *E. coli* cells can be packaged in groups of ten so that each package contains 100 *E. coli* cells.

Subsequently, the balls may be put to use in a particular application by opening the package that contains the ball and then tipping the container upside down so that is preferably mixed or agitated to assist with rehydration of the ball. Where the ball is added to a dry sample, such as the surface of an agar plate, a volume of liquid such as water may then be added to the plate to rehydrate the ball. In the case of the ball being contained in a vessel such as a vial or test tube, a sample of liquid may be added to the vessel and the experimentation or analysis to be conducted carried out in such vessel. While not as preferable, the invention also contemplates the addition of a liquid to the packaging followed by transfer of the sample, containing the rehydrated ball, to an appropriate vessel.

The freeze-dried product prepared according to the invention may be suitable for use in a number of commercial and/or research applications (for example, applications pertaining to microbiology, molecular biology, cell biology, biochemistry, biotechnology, medicine, and the food and beverage industry). In particular, in those applications where it is desirable to have control over the number of bioparticles present.

One particular application to which the balls of the invention may be put is in the testing of water samples for the presence of E. coli Traditionally, during such testing, QC steps are conducted which involve adding a known number of E. coli to a water sample and then analysing the sample. Current protocols for preparing a QC sample involve preparing a suspension of E coli and then performing an analysis to estimate the number of E. coli per ml of liquid. An aliquot of this suspension is then used in the testing procedure. As it will be appreciated, this known procedure may suffer from experimental artefacts due to the fact that one cannot determine with accuracy the exact number of E. coli cells present in the sample used, and also based on the loss of E. coli cells due to adhesion to surfaces of manipulation apparatus, such as pipettes. Alternative techniques involve a water sample being seeded with a freeze-dried sample of E. coli. These freeze-dried E. coli samples, which are commercially available, do not contain accurate numbers of E. coli and are not in a format that can be easily manipulated without loss of E. coli cells due to adhesion of cells to surfaces. The use of the balls of the present invention may introduce accuracy into QC procedures as precise numbers of organisms will be able to be added to a quality control sample and not lost during manipulation.

A further example of an application to which the balls of the invention may be put is in internal quality control (IQC) techniques used in microbiology. Such techniques are relatively new. One such procedure is described in PCT/AU00/00896 and involves the addition of an exact number of modified microorganisms to a sample before analysis. The microorganisms are modified to ensure that they can be easily differentiated from microorganisms that are present in the sample. For example, a green fluorescent protein (GFP) gene may be inserted into the organisms so that they can be differentiated from microorganisms present in the sample by their fluorescent properties. Use of the balls of the present invention may overcome problems associated with the format in which the modified microorganisms are presently used. For example, liquid samples, which may contain accurate numbers of a particular modified organism, invariably suffer from loss of activity during manipulation.

The freeze-dried balls of the present invention may also have specific application in delivery systems for oral vaccines. The use of the balls in this application would enable exact numbers of microorganisms or antigens to be administered to a subject, with no loss of microorganisms or antigens during administration of the vaccine. Similarly, the product of the invention may find application in the delivery of probiotics or prebiotics to a subject.

Further, the inventors contemplate the product of the invention to have direct application in the in vitro fertilization (IVF) industry. The product of the invention would enable simple manipulation of precise numbers of sperm, embryos and eggs.

The food and beverage industry is also likely to benefit from the use of the balls of the invention, particularly where microorganisms are used as starter cultures. For example, the fermentation of food, beer and wine would benefit from the use of technology that allows addition of exact numbers of microorganisms, allowing the introduction of a greater level of reproducibility in the fermentation process.

Biotechnology processes that involve the growth of cells, bacteria or other bioparticles would benefit from the use of the present technology. For example, the production of recombinant proteins from prokaryotic or eukaryotic cells may often be problematic resulting in differing yields of protein from one culture to another. While problems may stem from a number of factors involved in the culturing, expression, and harvesting process, the fact that a culture is seeded with an inconsistent quantity of recombinant cells may be considered one such problem. Accordingly, seeding an initial culture with a ball of the present invention, which ball contains a quantum of the recombinant cells, may alleviate one variable in the process.

The present invention is also suitable for preparing products containing a quantum of one or more genes or parts of genes for molecular biological applications. The bioparticle may be in the form of a host microorganism, cell vector containing a known number or type of gene or nucleic acid molecule. In this form, viability of the microorganism is not necessarily required. In some situations, the inventors contemplate the use of inactivated or dead microorganisms or cells in the solid product according to the invention. The product can be used to add a defined number of bioparticle to a gene related assay.

EXAMPLES

Example 1

Production of Products Using a Electrostatic Cell Sorter

Preparation of E. coli

A strain of E. coli (NCTC 9001) was grown at 37° C. for 24 hours in 1.6% (w/v) tryptone and 1% (w/v) yeast extract at pH 7.2. The cells were diluted 1 in 1000 in filtered (0.22 µm) phosphate buffered saline (PBS) (Sigma Chemical Company, Sydney, NSW) and analysed immediately.

Analysis of E. coli

The sample of E. coli was analysed using a Becton Dickinson FACStarplus flow cytometer fitted with a 488 nm water cooled argon ion laser. A 100 µm nozzle was fitted and the cytometer set up for sorting according to the manufacturers instructions. Sheath fluid consisted of filtered (0.22 µm) PBS plus 4% (w/v) bovine serum albumin fraction V (Sigma Chemical Company at pH 7.4.

A region was defined on a scatter plot of Side scatter verses Forward scatter that contained the E. coli. This region was then used to sort the E. coli.

Selection of Desired E. coli

The cytometer was set, according to the manufacturers instructions, to sort samples of 300 E. coli cells.

Freezing and Freeze-Drying the Droplets

Droplets from the cytometer were collected into test tubes that contained liquid nitrogen. After collection of the droplets, the tubes were placed in a Dynavac FD12 freeze dryer and dried overnight at a vacuum of 2×10−1 Torr and a condenser temperature of −50° C.

The next day, the freeze-dried particles were removed from the freeze drier and individually placed onto nutrient agar plates (Oxoid, Australia), and 200 µl of sterile 0.9% saline was carefully pipetted onto each ball. The balls were allowed to rehydrate for 5 min and then spread with a sterile plastic spreader. After incubation at 37° C. for 12 hours the agar plates were examined and were observed to contain between 250 and 300 *E. coli* colonies.

Example 2

Production of Products that Contain a Quantum of Viable *E. coli* Cells

Preparation of *E. coli*

A strain of *E. coli* (NCTC 9001) was grown at 37° C. for 24 hours in 1.6% (w/v) tryptone and 1% (w/v) yeast extract at pH 7.2. The cells were diluted 1 in 1000 in filtered (0.22 µm) PBS and analysed immediately.

Analysis of *E. coli*

The sample of *E. coli* was analysed using a Becton Dickinson FACScalibur flow cytometer that had been modified to enable 30 cells to be dispensed within a single droplet. Serum was injected into the droplet whilst it was forming to enable production of a droplet that freeze dries into a spherical mass without modifying the flow cytometer's sheath fluid.

The cytometer modification involved inserting, into the capture tube within the flow cell, a length of hypodermic tubing (A-M Systems, Calsborg, USA). A length of silicon tubing was connected to the hypodermic needle (A-M System, Calsborg, USA). A length of hypodermic tubing was connected to other end of the silicon tubing (A-M System, Calsborg, USA). The drop is formed in a droplet nozzle into which the hypodermic tubing from the cytometer is inserted. When the cytometer is turned on, drops are formed at the end of the hypodermic tubing from the nozzle.

A peristaltic pump (Cole Parmer Instruments, Illinios, USA) was used to inject horse serum through length of hypodermic tubing (A-M System, Calsborg, USA), which was also inserted into the droplet nozzle so that the serum can be mixed with the output of the flow cytometer to form drops. The flow rate of the pump was adjusted to match the flow rate of the fluid exiting the cytometer sort line.

To control the beginning of droplet formation a micro bore double acting pneumatic cylinder (Asco, Frenches Forest, NSW, Australia) was used with an attached polypropylene vacuum nozzle. The vacuum nozzle attached to the end of the shaft of the cylinder was held near the droplet nozzle exit point. The vacuum nozzle ensures that all liquids received from the droplet nozzle are sent to waste before droplet formation begins. On activation of the double acting cylinder, the vacuum nozzle is removed therefore allowing a droplet form.

A region was defined on a scatter plot of Side scatter verses Forward scatter that contained the *E. coli*. This region was then used to sort the *E. coli*.

Selection of Desired *E. coli*

The cytometer was set, according to the manufacturers instructions, to sort samples of 30 *E. coli* cells. The flow rate and the concentration of the *E. coli* were adjusted to ensure that the sort rate was between 150 and 200 sorts per second.

Freezing and Freeze-Drying the Droplets

Droplets from the cytometer were collected into test tubes that contained liquid nitrogen. After collection of the droplets, the tubes were placed in a Dynavac FD12 freeze dryer and dried overnight at a vacuum of 2×10−1 Torr and a condenser temperature of −70° C.

The next day, the vials were capped under vacuum and removed from the freeze drier. The vials were opened and the balls individually placed onto nutrient agar plates (Oxoid, Australia), and 200 μl of sterile 0.9% saline was carefully pipetted onto each ball. The balls were allowed to rehydrate for 5 min and then spread with a sterile plastic spreader. After incubation at 37° C. for 12 hours the agar plates were examined and were observed to contain between 25 and 30 *E. coli* colonies.

Example 3

Production of Balls that Contained a Quantum of *Bacillus Subtilis* Cells Containing a Single Copy of a Green Fluorescent Protein (GFP) Gene The ability to provide a sample which contains a defined number of genes will be particularly useful in molecular biological assays. In this situation, the bioparticle can be a microorganism which harbours a known number of copies of a particular gene. The gene maybe in one or more vectors in the microorganism, or incorporated in the genome of the microorganism.

Preparation of *Bacillus subtilis*

A strain of *Bacillus subtilis* (1049 Pxyl rpsB-GFP) was grown in nutrient broth plus 1% (w/v) xylose at 37° C. for 12 hours. This strain contained a single copy of the green fluorescent protein gene (GFP) under the control of a xylose promoter. The sample was diluted 1 in 1000 into filtered (0.22 μm) PBS plus 1% (w/v) xylose.

Analysis of *Bacillus subtilis*

The sample of *Bacillus subtilis* was analysed using a modified Becton Dickinson FACScalibur flow cytometer as in example 2.

A region was defined on a scatter plot of green fluorescence (FL1) verses Forward scatter that contained the *Bacillus subtilis*. This region was then used to sort *Bacillus subtilis* spores.

Selection of Desired *Bacillus subtilis*

The cytometer was set, according to the manufacturers instructions, to sort samples of 30 *Bacillus subtilis* cells. The flow rate and the concentration of *Bacillus subtilis* were adjusted to ensure that the sort rate was between 200 and 220 sorts per second.

Freezing and Freeze-Drying the Droplets

Droplets were collected into glass freeze drying vials that contained liquid nitrogen. After collection of the droplets, the vials were capped with the caps halfway inserted and placed in a Dynavac FD12 freeze dryer and dried overnight at a vacuum of 2×10−1 Torr and a condenser temperature of −70° C.

The next day, the freeze-dried balls were removed from the freeze drier and individually placed onto nutrient agar plates (Oxoid, Australia) which had been spiked with 200 μl of a sterile solution of 1% (w/v) xylose. Sterile saline solution (200 μl) was carefully pipetted onto each ball. The balls were allowed to rehydrate for 30 seconds and then spread with a sterile plastic spreader. After incubation at 37° C. for 12 hours the agar plates were examined and were observed to contain between 25 and 30 *Bacillus subtilis* colonies.

The plates were examined under a UV light and each colony was observed to fluoresce green. This demonstrated that each *Bacillus subtilis* cell within the ball contained the GFP gene.

Example 4

Production of Balls that Contain a Quantum of Viable *Bacillus cereus* Spores Preparation of *B. cereus* Spores A strain of *B. cereus* (ATCC 10876) was grown for 7 hours in nutrient broth (Oxoid, CM1) at 37° C. A 1 ml aliquot of the *B. cereus* culture was spread on a nutrient agar plate (Oxoid, Australia) and allowed to dry at room temperature for 24 hours. Once a visible lawn of growth was observed covering the plate, the plate was incubated at 37° C. for 48 hours.

The resulting spore culture lawn was removed from the agar plate with a 10 µl sterile loop and suspended in 1.5 ml sterile de-ionised water. The spore suspension was washed four times by repetitive centrifugation (6,200 rpm, 2 minutes) and re-suspended in 1.5 ml de-ionised water. The final spore pellet was suspended in 1 ml Isoton II (Beckman Coulter) and stored at 2-8° C.

A series of dilutions of the spore preparation in Isoton II (Beckman coulter) were analysed on the Becton Dickinson FACScalibur flow cytometer. The optimal spore concentration was determined by ensuring the cytometer was detecting between 1500 and 2000 events per second.

Staining of *B. cereus* Spores

A 20 µl aliquot of the prepared spore suspension was diluted in 400 µl Isoton II (Beckman Coulter). Syto 11 green fluorescent nucleic acid stain (Molecular Probes, Eugene, USA) was added to the diluted spore suspension to give a final concentration of 0.0005 mM. The suspension was then incubated at room temperature for 30 minutes.

Analysis of *B. cereus*

The sample of *B. cereus* spores was analysed using a modified Becton Dickinson FACScalibur flow cytometer as described in example 2.

Selection of Desired *B. cereus*

The cytometer was set, according to the manufacturers instructions, to sort samples of 33 *B. cereus* cells. The flow rate and sort region were adjusted to ensure that the sort rate was between 200 and 250 sorts per second.

Freezing and Freeze-Drying the Droplets

Droplets from the cytometer were collected into freeze dry vials that contained liquid nitrogen. Control plates were prepared by collecting single drops onto nutrient agar plates. This enabled enumeration of the viable spores that were being sorted (see Table 1). The vials containing the frozen drops were placed in a Dynavac FD12 freeze dryer and dried overnight at a vacuum of 2×10−1 Torr and a condenser temperature of −70° C. The next day the vials were sealed under vacuum and then crimped.

Rehydration and Evaluation

The vials were opened and the freeze-dried balls were individually tipped onto nutrient agar plates (Oxoid, Australia), and 200 µl of sterile 0.9% saline was carefully pipetted onto each ball. The balls were allowed to rehydrate for 1 min and then the plate was rotated to allow the rehydration liquid and dissolved freeze-dried ball to spread across the plate. After incubation at 37° C. for 8 hours, the agar plates were examined and were observed to contain between 28 and 33 *B. cereus* colonies. The mean colony forming unit (cfu) for 15 re-hydrated *B. cereus* freeze-dried balls was 30.1 with a standard deviation of 1.7 (Table 1).

The counts for the control plates were similar to the counts for the re-hydrated freeze dried balls (Table 1) indicating that all spores that were sorted survived the freeze drying process. The reason that 33 viable spores were not sorted every time was probably due to the cytometer occasionally sorting debris material, non-viable spores or non-viable cells. This could probably be overcome by producing a more pure spore preparation.

TABLE 1

Control data and post freeze drying recovery of *B. cereus* from freeze-dried balls

| Sample No | Control plates (cfu) | Re-hydrated balls (cfu) |
|---|---|---|
| 1 | 30 | 31 |
| 2 | 31 | 31 |
| 3 | 31 | 33 |
| 4 | 30 | 32 |
| 5 | 30 | 32 |
| 6 | 28 | 30 |
| 7 | 31 | 30 |
| 8 | 29 | 29 |
| 9 | 30 | 27 |
| 10 | 31 | 30 |
| 11 | 27 | 28 |
| 12 | 27 | 31 |
| 13 | 31 | 28 |
| 14 | 30 | 29 |
| 15 | 31 | 30 |
| Mean | 29.8 | 30.1 |
| Standard deviation | 1.4 | 1.7 |

Stability of *B. cereus* Freeze-Dried Balls

The stability of the freeze dried balls that contained *B. cereus* spores was tested by storing the sealed vials at 4° C., 22° C. and 37° C. respectively and then rehydrating the balls on nutrient agar plates. Two different batches were produced and tested (Tables 2 & 3). No reduction in recovery of viable *B. cereus* was observed after storage for 33 days at 37° C., after 21 days at 4° C. and after 33 days at 20° C.

TABLE 2

Stability data for storage at 20° C. and 37° C.

| Sample No | Pre-freeze drying controls (cfu) | Re-hydrated Day 0 (cfu) | Re-hydrated Day 33 (22° C.) (cfu) | Re-hydrated Day 33 (37° C.) (cfu) |
|---|---|---|---|---|
| 1 | 26 | 28 | 30 | 30 |
| 2 | 25 | 30 | 28 | 25 |
| 3 | 27 | 30 | 30 | 26 |
| 4 | 29 | 29 | 29 | 29 |
| 5 | 26 | 30 | | |
| 6 | 25 | 28 | | |
| 7 | 26 | 29 | | |
| 8 | 27 | 30 | | |
| 9 | 28 | 29 | | |
| 10 | 22 | 30 | | |
| Mean | 26.1 | 29.3 | 29.3 | 27.5 |
| Standard Deviation | 1.9 | 0.8 | 0.96 | 2.4 |
| % survival | | 112% | 112% | 105% |

TABLE 3

Stability data for storage at 4° C.

| Sample No | Pre-freeze drying controls (cfu) | Re-hydrated Day 21 (cfu) |
|---|---|---|
| 1 | 25 | 27 |
| 2 | 27 | 24 |
| 3 | 29 | 27 |
| 4 | 24 | 26 |
| 5 | 29 | 26 |
| Mean | 26.8 | 26 |
| Standard deviation | 2.3 | 1 |
| % survival | | 97% |

Example 5

Production of Balls that Contained a Quantum of 8 μm Beads Coated with Viable *E. coli*

Preparation of E. coli

A strain of *E. coli* (NCTC 9001) was grown at 37° C. for 24 hours in 1.6% (w/v) tryptone and 1% (w/v) yeast extract pH 7.2. The cells were washed in filtered (0.22 μm) PBS and processed immediately.

Preparation of Beads

Amino modified magnetic beads with a diameter of 8 microns were supplied by Spherotch Inc. (Libertyville, Ill., USA). A 1 ml aliquot of the beads was washed three times in PBS with a magnetic concentrator (Spherotech) according to the manufacturers instructions. The beads were resuspended in 35% (v/v) glutaraldehyde (Sigma) in PBS, vortexed for 2 minutes and incubated at room temperature on a rotary mixer for 2 hours. The beads were then washed four times in PBS, resuspended in 1 ml of PBS and vortexed for 2 minutes.

Coating Beads with *E. coli*

A 20 μl aliquot of the bead preparation was mixed with 1 ml of washed *E. coli* cells at an approximate concentration of $1 \times 10^8$ per ml. The sample was then incubated on a rotary mixer at room temp for 30 minutes.

Staining *E. coli* Coated Beads

A 20 μl aliquot of the prepared spore suspension was diluted in 400 μl Isoton II (Beckman Coulter). Syto 16 green fluorescent nucleic acid stain (Molecular Probes, Eugene, USA) was added to the diluted spore suspension to give a final concentration of 0.0005 mM. The suspension was then incubated at room temperature for 30 minutes.

Analysis of Coated Beads

The stained bead sample was analysed using a modified Becton Dickinson FACScalibur flow cytometer as in Example 2.

A region was defined on a scatter plot of green fluorescence (FL1) verses Forward scatter that contained the *E. coli* coated beads.

Selection of Desired *Bacillus subtilis*

The cytometer was set, according to the manufacturers instructions, to sort samples of 30 *E. coli* coated beads. The flow rate and the concentration of the stained beads were adjusted to ensure that the sort rate was between 200 and 220 sorts per second.

Freezing and Freeze-Drying the Droplets

Droplets were collected into glass freeze drying vials that contained liquid nitrogen. After collection of the droplets, the vials were capped with the caps halfway inserted and placed in a Dynavac FD12 freeze dryer and dried overnight at a vacuum of $2 \times 10-1$ Torr and a condenser temperature of −70° C.

The next day, the freeze-dried balls were removed from the freeze drier and rehydrated, incubated and the colonies counted as described in Example 2.

After incubation at 37° C. for 12 hours the agar plates were examined and were observed to contain between 25 and 30 *E. coli* colonies.

Example 6

Production of Balls that Contained a Quantum of *Bacillus cereus* Spores Produced Without Using a Flow Cytometer Preparation of *B. cereus* Spores A strain of *B. cereus* (ATCC 10876) was grown on nutrient agar (Oxoid, Australia) at 37° C. for 24 hours and then kept at room temperature for 1 week. Spores were washed from the culture plate with PBS and stored at 4° C.

Dilution of Spores

Spores were diluted in PBS to an approximate concentration of $1\times10^7$ spores per ml and stored at 4° C. This stock dilution was then serially diluted in horse serum and a burette was used to place 1 drop from each dilution onto three nutrient agar plates. The burette was used to produce drops because drops with a more reproducible volume were found to be obtained than when pastuer pipettes were used.

The drop was spread using a plastic spreader, the plates incubated at 37° C. overnight and colonies counted. The colony counts were used to calculate the dilution of the spore stock that was required to produce approximately 30 colonies in one drop.

Production of Balls

The spore stock was diluted in horse serum to a concentration that was expected to produce 30 cfu in a single drop. Drops of the diluted spore suspension were dropped into a bowl of liquid nitrogen and allowed to freeze. Frozen balls were transferred to freeze drying vials and freeze dried as detailed in Example 3.

Rehydration and Evaluation

The next day, the freeze-dried balls were removed from the freeze drier and individually placed onto nutrient agar plates (Oxoid, Australia), and 200 μl of sterile 0.9% saline was carefully pipetted onto each ball. The balls were allowed to rehydrate for 1 min and then the plate was rotated to allow the rehydration liquid and dissolved freeze-dried ball to spread across the plate. After incubation at 37° C. for 8 hours, the agar plates were examined and the number of colonies recorded (Table 4). The plates were observed to contain between 30 and 58 colonies. The mean cfu for 15 re-hydrated *B. cereus* freeze-dried balls was 40.3 with a standard deviation of 7.8.

TABLE 4

| Colonies | 30 | 33 | 42 | 40 | 36 | 44 | 44 | 39 | 39 | 58 | 44 | 54 | 41 | 31 | 30 |
|---|---|---|---|---|---|---|---|---|---|---|---|---|---|---|---|
| Mean | 40.3 | | | | | | | | | | | | | | |
| Std Dev | 7.8 | | | | | | | | | | | | | | |

Stability of *B. cereus* Freeze-Dried Balls

Freeze-dried balls containing a mean of 30 *B. cereus* spores produced between 93 and 99% recovery of spores. Two batches of *B. cereus* freeze-dried balls produced 93% spore recovery after 33 days at 37° C., 97% spore recovery after 21 days at 4° C. and 99% spore recovery after 33 days at 20° C.

Example 7

Production of a Large Quantum of *E. coli*

Preparation of *E. coli*

A strain of *E. coli* (ATCC 11775) was grown in nutrient broth (Oxoid, Australia) at 37° C. for 12 hours.

Freezing and Freeze-Drying the Droplets

A glass pasteur pipette was used to drop droplets of *E. coli* broth culture into a beaker of liquid nitrogen. The frozen droplets were collected using a sieve and placed into a chilled (−20° C.) glass freeze-drying vessel.

The frozen droplets were placed in a Dynavac FD12 freeze dryer and dried overnight at a vacuum of $2 \times 10^{-1}$ Torr and a condenser temperature of −70° C.

The next day, the freeze-dried balls were removed from the freeze drier and individually placed into nutrient broth (as detailed above). After incubation at 37° C. for 12 hours the tubes were examined and were observed to contain viable cultures of *E. coli*.

Comments

The technology of the present invention may be put to applications which may not require a small quantum of the bioparticles to be present in each ball or within a group of balls. One such example is in oral vaccination applications. In such application balls containing an approximate number of bioparticles (e.g. between $5 \times 10^5$ and $1 \times 10^6$) may be used.

According to the present embodiment, frozen balls containing a quantum of bioparticles are formed by allowing droplets of the suspension of bioparticles to fall into a cryogenic liquid as described above. The droplets may be formed by forcing an appropriate suspension of bioparticles through any suitable orifice. For example, this step may be performed using a peristaltic pump connected to a pastuer pipette. Those skilled in the art will appreciate alternative means by which such droplets may be formed. Where a flow cytometry apparatus has been employed to analyse and select the bioparticles, quantities of bioparticles may be expressed therefrom by known means.

As with the previously described embodiment of the invention, the droplets which are formed are allowed to fall into a cryogenic liquid to form a frozen ball of bioparticles.

The frozen balls contained within the cryogenic liquid may then be subjected to a freeze drying procedure as described above to form the balls of the invention. Freeze-dried balls may be packaged, stored, and prepared for use as previously described.

As will be appreciated, suspension and growth media's, temperatures, and other conditions of the process according to the present embodiment of the invention may be optimised to the needs of a particular bioparticle and the application to which the final product may be put. Generally, the conditions should be such that the viability or stability of the bioparticles is maintained during processing.

As with the previously described embodiment of the invention, quality control steps may be conducted post formation of the balls produced in accordance with the present embodiment. In this form of the invention, quality control steps may include: counting the number of bioparticles contained within selected samples of the product by analytical methods such as culturing the bioparticles on agar plates, or by flow cytometry, or by nucleic acid based analytical methods such as the polymerase chain reaction (PCR), or measurement of the uniformity of the product, for example by weighing or measuring the size of selected balls.

The product of this alternative embodiment of the invention may be used in various applications, for example vaccination applications, microbiological applications, or applications pertaining to molecular biology, where an estimate of the number of bioparticles within the product is sufficient to reach a desired end.

The invention has been described herein, with reference to certain preferred embodiments, in order to enable the reader to practice the invention without undue experimentation. However, a person having ordinary skill in the art will readily recognise that many of the components and parameters may be varied or modified to a certain extent without departing from the scope of the invention. Furthermore, titles, headings, or the like are provided to enhance the reader's comprehension of this document, and should not be read as limiting the scope of the present invention.

The present invention allows the production of batches of products that contain a known and substantially identical number of a bioparticle. The present inventors have consistently shown the method of the invention can produce a product having a known number of a bioparticle within around 7% standard deviation. In addition, the product in its freeze-dried form can be handled easily without the concern of loss or shedding of the bioparticle present. To use or retrieve the bioparticle from the product, all that is required is to add a liquid to the product. In order to ensure that the actual number of bioparticle is used, the product can be added in its dry form to a test and then rehydrated with a suitable liquid. The product can be moved to different vessels in its dry form without the concern that some of the bioparticle will remain in the original vessel. This is a clear advantage over the prior art.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A process for forming a solid product containing a defined small number of a viable bacteria, the process comprising:

providing bacteria in suspension;

selecting a defined number of the bacteria of between 5 and 1000 in a drop using a flow cytometer to sense a bacterium;

adding the drop containing the bacteria to liquid nitrogen to form a frozen ball containing the defined number of the bacteria; and subjecting the frozen ball to freeze-drying to form a substantially dry solid product containing the defined number of the bacteria, wherein the product is capable of being transferred between containers in its solid form without loss of the bacteria, and wherein the product is capable of releasing the defined number of viable bacteria in a liquid, and wherein the defined number of the bacteria in the product when measured in two or more replicates is within a standard deviation of less than about 10% of the desired number of bacteria.

2. The process according to claim 1 wherein the bacteria are selected from the group consisting of *Legionella, Salmonella, Leptospirosis, Escherichia, Saccharomyces, Clostridium, Vibrio, Pseudomonas, Bacillus, Streptomyces, Staphylococcus, Enterobacter, Listeria, Candida, Zygosaccharomyces,* and mixtures thereof.

3. The process according to claim 2 wherein the bacteria are *Escherichia coli* or *Bacillus cereus*.

4. The process according to claim 1 wherein the product contains a defined number of bacteria of between 10 and 100.

5. The process according to claim 4 wherein the product contains a defined number of bacteria of 30.

6. The process according to claim 1 wherein the defined number of the bacteria in the product is within a standard deviation of 5% or less.

7. The process according to claim 1 wherein the defined number of the bacteria in the product is within a standard deviation of 2%.

8. The process according to claim 1 wherein the bacteria are captured in a drop from 0.001 ml to 1 ml prior to freezing.

9. The process according to claim 6 wherein the drop is about 0.1 ml.

10. A product comprising a defined number of viable bacteria made in accordance with the process according to claim 1.

* * * * *